United States Patent [19]

Hattori et al.

[11] Patent Number: 5,048,331
[45] Date of Patent: Sep. 17, 1991

[54] CONTINUOUS RAINWATER MONITORING SYSTEM

[75] Inventors: Nobuyoshi Hattori; Takaaki Fukumoto, both of Itami, Japan

[73] Assignee: Mitsubishi Denki Kabushiki Kaisha, Japan

[21] Appl. No.: 517,314

[22] Filed: May 1, 1990

[30] Foreign Application Priority Data

Jan. 25, 1990 [JP] Japan .................................. 2-13638

[51] Int. Cl.⁵ ............................................ G01W 1/14
[52] U.S. Cl. .................................... 73/170 R; 73/171
[58] Field of Search ............... 73/170 R, 171, 863.02; 324/439

[56] References Cited

U.S. PATENT DOCUMENTS

| | | | |
|---|---|---|---|
| 4,569,224 | 2/1986 | Fukumoto et al. | 73/32 R |
| 4,600,888 | 7/1986 | Fukumoto et al. | 324/439 |
| 4,624,834 | 11/1986 | Fukumoto | 422/90 |
| 4,665,743 | 5/1987 | Masniere et al. | 73/171 |

Primary Examiner—Charles A. Ruehl
Attorney, Agent, or Firm—Leydig Voit & Mayer

[57] ABSTRACT

A continuous rainwater monitoring device for effecting automatic chemical analysis of the rainwater. The device comprises, in addition to a funnel-shaped receiver-container, a rain gauge, a measurement and analysis means, and an automatic recorder, the following: a showering ring disposed above the receiver-container and supplied with a cleaning water from a cleaning water source; a cleaning evaluation means including an electrical resistivity meter; and a rainfall sensor for detecting the commencements and ends of rainfalls. During the time when there is no rainfall, the receiver-container and the rain gauge are filled with cleaning water supplied from the cleaning water source via the showering ring. When a commencement of a rainfall is detected by the rainfall sensor, the stored cleaning water is discharged via the cleaning evaluation means and the measurement of the amount of the rainfall and the chemical analysis of the rainwater are effected automatically and periodically by the rain gauge and the measurement and analysis means, respectively. When an end of the rainfall is detected, the receiver-container and the rain gauge are cleaned of contaminants by means of the cleaning water supplied from the showering ring; the cleaning continues until the resistivity of the used cleaning water as determined by the cleaning evaluation means falls for example below 5 Ω·cm. After the cleaning is finished, the receiver-container and the rain gauge are filled with the cleaning water, to wait for the commencement of the next rainfall.

8 Claims, 2 Drawing Sheets

CONTINUOUS RAINWATER MONITORING SYSTEM

BACKGROUND OF THE INVENTION

This invention relates to continuous rainwater monitoring devices, which are capable of continuous quantitative evaluation of the contents, such as hydrogen ions and other ionic substances, etc., contained in the rainwater.

In recent years, acid rain has become a world wide problem, on account of their adverse effects on forests and lakes, and further, on flora and fauna thereof.

A device as shown in FIG. 1 has been known as a rainwater monitoring device for the measurement of the pH values of the rainwater, and is utilized for the purpose of investigating and researching the problem of acid rain. The device of FIG. 1 comprises the following: a funnel-shaped water receiver 101 for receiving the rainwater; a reservoir 102 disposed thereunder for storing the rainwater collected by the receiver; and a pH sensor 103 for analysing the pH value of the rainwater stored in the reservoir 102. The receiver 101 and the reservoir 102 are placed outdoors during rainfalls for sampling the rainwater. The rainwater thus sampled is supplied to the pH sensor 103 as the specimen material for the measurement of the pH value of the rainwater. After the measurement is made, the water receiver 101 and the reservoir 102 are cleaned manually.

The above-described conventional rainwater monitoring device has the following disadvantages. Since the measurements, as well as the cleaning operations after the measurements, are all effected manually by personnel, the device not only incurs personnel expenses, but has the problems that the cleaning of the measurement containers such as the receiver 101 and the reservoir 102 tend to be insufficient, and errors in the measured values tend to be great due to variations in the cleanliness of the reservoir 102 and the receiver 101 after they are cleaned. Namely, for measurements of extremely high precision, thorough cleaning of the measurement containers for the rainwater is essential. To this end, it is necesary to effect exact evaluations of the cleaning operations of the measurement containers after the cleaning. For effecting such exact cleaning evaluations, it is necessary to clean under identical conditions the measurement containers for the rainwater on the one hand, and the evaluation containers for the cleaning water on the other, which are for evaluating the contamination states of the cleaning water that has been used in cleaning the measurement containers for the rainwater. When, however, the cleaning is effected manually, it is extremely difficult to control the cleaning conditions to be exact as is required. Thus, cleaning evaluations may be completely omitted, or, even when cleaning evaluations are effected, they tend to be far from sufficient since the cleaning conditions as mentioned above are not controlled exactly.

Recently, the need for taking preventive measures against acid rains and for suppressing occurences of acid rains are becoming increasingly apparent. For effecting these, it is necessary to analyse the ionic contents, ect., of the rainwater for the purpose of investigating and determining the rainfall regions of the acid rains or the frequencies thereof, so that the sources of release of contaminants can be specified on the basis of the analyses. For such analysis, it is necessary to enhance the measurement sensitivity such that trace amounts of ions at the level of a few ppb (parts per billion) to a few hundred ppb can be detected; however, the above conventional rainwater monitoring device falls far short of meeting such requirements.

SUMMARY OF THE INVENTION

It is therefore a primary object of this invention to provide a continusous rainwater monitoring device which is capable of effecting automatically, continuously, and at an extremely high precision, the measurement of the pH value of rainwater, the analysis of the contents and the measurement of the concentration of ions contained therein, and the cleaning and the cleaning evaluation of the system after each measurement, so that reduction of personnel costs and the enhancement of the precision and reliability of the measurements and analyses are accomplished sumultaneously.

The above object is accomplished in accordance with the principle of this invention in a continuous rainwater monitoring device which comprises the following: a rainfall sensor for detecting a commencement and an end of each occurrence of rainfall; a receiver-container for receiving and collecting rainwater; a rain gauge for storing the rainwater collected by the receiver-container, and for determining the amount of rainfall by the measurement of the rainwater; a measurement and analysis means for analysing ionic chemical characteristics, including pH, of the rainwater collected in the rain gauge; an automatic recorder for automatically recording results of the measurements and analyses effected by the measurement and analysis means; a cleaning means for cleaning interiors of the receiver-container means and rain gauge means by means of cleaning water, so as to remove contaminants attached thereto; and a cleaning evaluation means for evaluating cleanliness of the interiors of the receiver-container and the rain gauge, wherein the cleaning evaluation means collects the cleaning water that has been utilized in cleaning the receiver-container and the rain gauge, so as to evaluate the state of contamination of the used cleaning water, letting the cleaning means continue the cleaning operation until the contamination state falls below a predetermined state.

In a preferred form, the monitoring device operates as follows: During the time when there is no rainfall, the receiver-container and the rain gauge are filled with cleaning water supplied from the cleaning means. When a commencement of a rainfall is detected by the rainfall sensor, the stored cleaning water is discharged via the cleaning evaluation means and the measurement of the amount of the rainfall and the chemical analysis of the rainwater are effected automatically by the rain gauge and the measurement and analysis means, respectively. When an end of the rainfall is detected, the receiver-container and the rain gauge are cleaned of contaminants by means of the cleaning water supplied from the cleaning means; the cleaning continues until the state of contamination of the used cleaning water as determined by the cleaning evaluation means falls below the predetermined level. After the cleaning is finished, the receiver-container and the rain gauge are filled with the cleaning water, to wait for the commencement of the next rainfall.

The novel features which are believed to be characteristic of this invention are set forth with particularity in the appended claims. This invention itself, however, both as to its organization and method of operation, together with further objects and advantages thereof may best be understood by reference to the following detailed description taken in connection with the accompanying drawings.

BRIEF DESCRIPTION OF THE DRAWINGS

In the drawings, like reference numerals represent like parts.

DETAILED DESCRIPTION OF THE PREFERRED EMBODIMENT

Figure 1:
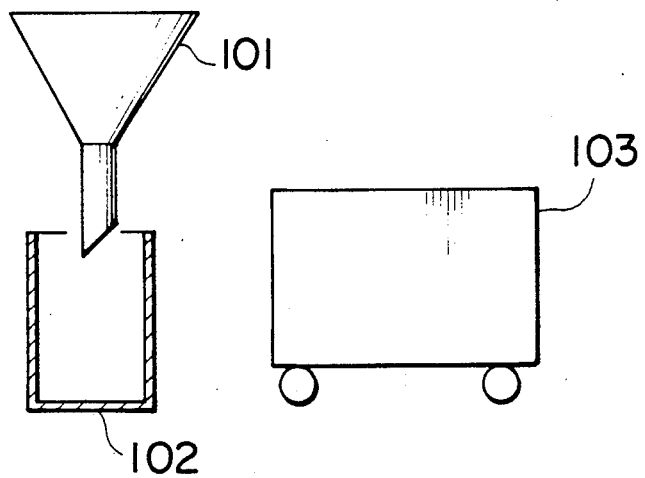
FIG. 1. is a schematic view of a conventional rainwater monitoring device.
Figure 2:
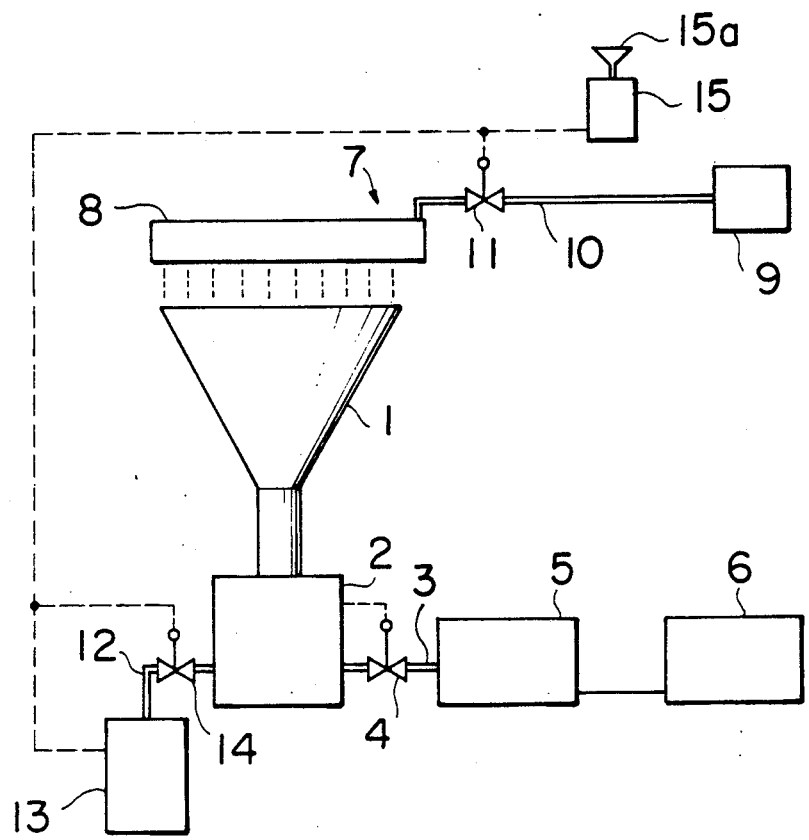
FIG. 2 is a block diagram of a continuous rainwater monitoring device according to this invention, showing an overall organization thereof.
Figure 3:
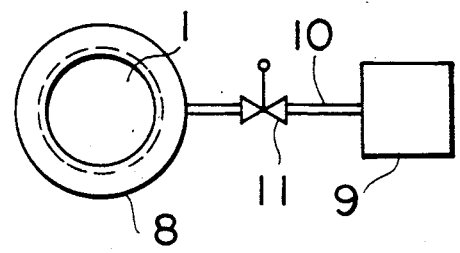
FIG. 3 is a top view of a portion of the device of FIG. 2

Referring now to FIGS. 2 and 3 of the drawings, an embodiment of this invention is described. As shown in FIG. 2, the monitoring device according to this invention comprises a funnel-shaped water receiver-container 1, to which a rain gauge 2 is coupled thereunder. To this rain gauge 2 is coupled, via a pipe 3 having a valve 4 interposed at an intermediate portion thereof, a measurement and analysis means 5 which may comprise for example, a Ph sensor and an ion chromatograph. To the measurement and analysis means 5 is coupled an automatic recorder 6, which automatically records the results of the measurement and analysis outputted from the measurement and analysis means 5.

Further, above the water receiver-container 1 is disposed a cleaning means, generally designated by reference numeral 7, which comprises the following: a showering ring 8 which consists, for example, of a doughnut-shaped pipe, etc., as best shown in FIG. 3; and a cleaning water source 9, which is coupled to the showering ring 8 via a pipe 10 having a valve 11 interposed at an intermediate portion thereof. The torus-shaped showering ring 8, through the central opening of which the rain may fall freely onto the receiver-container 1 (see FIG. 3), has a multitude of small through-holes formed at the bottom wall thereof along the circumferential direction; thus, the cleaning water supplied to the showering ring 8 from the water source 9 via the pipe 10 is sprayed onto the container-receiver 1 in the form of a shower. The geometric arrangement of the small through-holes and the diameter of the showering ring 8 are selected in such a manner that the cleaning water falling from the small through-holes in the form of a shower can clean, uniformly and without exception, the whole interior surface of the water receiver-container 1. The water source 9 stores cleaning water of an extremely high purity, such as ultra-pure water, whose electric conductivity is, generally speaking, not more than 0.1 $\mu$S/cm (microsiemens per centimeter).

On the other hand, to a lower portion of the rain gauge 2 is coupled, via an inverted L-shaped pipe 12, a cleaning evaluation means 13; at the middle of the pipe 12 is interposed a valve 14. In the case of this embodiment, the cleaning evaluation means 13 consists of a resistivity meter, which measures the electrical resistivity of the cleaning water supplied from the rain gauge 2 to the cleaning evaluation means 13 via the pipe 12, and thereby determines and evaluates the degree to which the cleaning of the receiver-container 1 and the gauge 2 has been accomplished by means of the cleaning water. Namely, when the resistivity of the cleaing water supplied to the cleaning evaluation means 13 is above a predetermined reference level (e.g., 5 K$\Omega$·cm), an evaluation is made that the water receiver-container 1 and the rain gauge 2 have been cleaned thoroughly; then, as described in detail below, the valve 14 is closed, and, after an interval of time at the end of which the water receiver-container 1 is filled with the cleaning water supplied from the source 9, the valve 11 is closed to stop the supply of cleaning water ot the water receiver-container 1. On the other hand, when the resistivity of the cleaning water supplied to the evaluation means 13 is below the predetermined level, it is judged that the cleaning has not yet been thoroughly accomplished, and the cleaning of the receiver-container 1 and the rain gauge 2 by means of the cleaning water supplied from the source 9 is continued. It is noted in passing that the cleaning water supplied to the evalutation means 13 is discharged therefrom to the outside after evaluation. These methods of operation will be explained in detail below.

The monitoring device of FIGS. 2 and 3 further comprises a rainfall sensor 15 for detecting the beginning and the end of each rainfall. The sensor 15, for example, detects the commencement and end of each rainfall as follows: It detects the commencement of a rainfall when the weight of rainwater which is collected in the water collector plate 15a during a predetermined period of time exceeds a predetermined value. On the other hand, it senses the end of a rainfall when the amount of increase per unit period of time of the weight of the rainwater that is collected in the plate 15a falls below a predetermined level. The output of the rainfall sensor 15 is electrically coupled to the controls of the valves 4, 11 and 14; thus, as described below, when the commencement of a rainfall is sensed, the valve 14 is opened to discharge the cleaning water stored in the receiver-container 1 and the rain gauge 2, to be subsequently closed shortly thereafter when the cleaning water stored in the receiver-container 1 and the rain gauge 2 is discharged to the outside. On the other hand, when the end of a railfall is detected, the valve 4 is closed and the valves 11 and 14 are opened to effect the cleaning operation; after the cleaning of the receiver-container 1 and the rain guage 2 is accomplished, the valve 14 is closed; the valve 11 is closed shortly thereafter when the receiver-container 1 is filled with cleaning water. These operations will become more clear below.

Let us now describe the method of operation of the above monitoring device shown in FIGS. 2 and 3.

Let us begin the description from the state of the device at a time when there is no rainfall. During the time when there is no rainfall, cleaning water (supplied from the source 9) is stored in the receiver-container 1 and the rain gauge 2, all the valves 4, 11, and 14 being maintained in the closed state, as will be made clear below. Thus, when a commencement of a rainfall is detected by the rainfall sensor 15, the valve 14 is opened to discharge to the outside (through the pipe 12 and the evaluation means 13) the cleaning water stored in the receiver-container 1 and the rain gauge 2; when the cleaning water in the receiver-container 1 and the rain gauge 2 is thus completely discharged, the valve 14 is closed again, so that the rainwater falling on the receiver-container 1 through the central opening of the doughnut-shaped showering ring 8 is collected by it and stored in the rain gauge 2, at which the amount of rainfall is measured periodically at a predetermined period. Each time a measurement of the amount of rainfall is completed, the valve 4 is opened to supply via the pipe 3 the rainwater within the rain gauge 2 to the measurement and analysis means 5, at which predetermined chemical measurements and analysis (such as the measurement of the pH value, the analyses of the concentrations and the components of the ions, etc.) are effected; the results of these measurements and analyses are recorded automatically by the automatic recorder 6. These measurements and analyses are repeated periodically at a predetermined period until the rainfall stops.

When the end of a rainfall is finally detected by the rainfall sensor 15, the valve 4 is closed and the valves 11 and 14 are opened. Thus, the cleaning water, such as ultra-pure water having an electrical resistivity of not less than 10 k$\Omega$·cm, which is supplied to the showering ring 8 from the source 9 via the pipe 10, is sprayed in the form of a shower onto the cone-shaped interior surface of the receiver-container 1 from the small through-holes formed at the bottom surface of the showering ring 8; the cleaning water thus falling on the cone-shaped surface of the receiver-container 1 flows down on the cone-shaped surface and thereby removes, evenly and without exception, any contaminants, such as ions, attached thereon; the cleaning water thereafter flows into the rain gauge 2, and after cleaning the interior thereof, is collected into the cleaning evaluation means 13 via the pipe 12. During the time when the cleaning is thus effected, the ceaning evaluation means 13 periodically measures the cleanliness, i.e., water quality, of the cleaning water; in the case of this embodiment, in which the evaluation means 13 consists of a resistivity meter, the resistivity of the cleaning water is measured for the purpose of dertermining the cleanliness, i.e., water quality, of the cleaning water. The cleaning operation is continued until the resistivity of the cleaning water determined by the evaluation means 13 reaches a predetermined value (e.g., 5 k$\Omega$·cm), which value means that the the interiors of the receiver-container 2 and the rain gauge 2 are fully and completely clean. When the resistivity of the cleaning water determined by the evaluation means 13 does reach the predetermined level, the valve 14 is closed first so as to fill the receiver-container 1 and the rain gauge 2 with the cleaning water supplied from the source 9; the valve 11 is closed after the receiver-container 1 and the rain gauge 2 is filled up with the cleaing water.

The device is kept in this state until the next commencement of a rainfall is detected by the rainfall sensor 15. Since the receiver-container 1 and the rain gauge 2 are filled with cleaning water during the intervals of fine weather (i.e., no rainfalls), the contamination of the receiver-container 1 and the rain gauge 2 from the outside environment during such fine weather intervals can be effectively prevented. It is further preferred, by the way, that the upper opening of the receiver-container 1 be closed by a lid during the fine weather intervals, so as to ensure the prevention of contamination of the receiver-container 1 and the rain gauge 2 during such intervals.

When the commencement of a next rainfall is detected by the rainfall sensor 15, the above series of operations are repeated from the state in which the cleaning water is stored in the receiver-container 1 and the rain guage 2, as described above at the outset. Thus, the measurements and analyses of the rainwater are effected automatically and continually whenever the fainfalls are detected.

While description has been made of a particular embodiment of this invention, it will be understood that many modifications may be made without departing from the spirit thereof; the appended claims are contemplated to cover any such modifications as fall within the true spirit and scope of this invention.

What is claimed is:

1. A continuous rainwater monitoring device comprising:
   rainfall sensor means for detecting the commencement and the end of each rainfall occurence;
   receiver-container means for receiving and collecting rainwater;
   rain gauge means for storing the rainwater collected by the receiver-container means and for determining an amount of rainfall by a measurement of the rainwater;
   measurement and analysis means for analysing ionic chemical characteristics, including the pH of the rainwater colleted in the rain gauge means;
   automatic recording means for automatically recording results of measurements and analyses effected by the measurement and analysis means;
   cleaning means for cleaning the interior of said receiver-container means and rain gauge means by means of cleaning water, so as to remove contaminants attached thereto; and
   cleaning evaluation means for evaluating the cleanliness of the interiors of the receiver-container means and the rain gauge means, wherein the cleaning evaluation means collects the cleaning water that has been utilized in cleaning the receiver-container means and the rain gauge means, so as to evaluate the state of contamination of said cleaning water, and continues to conduct a cleaning operation until the contamination state of the interiors of said receiver-container means and said rain gauge means falls below a predetermined level.

2. A monitoring device as claimed in claim 1, wherein said cleaning evaluation means comprises resistivity meter means for measuring an electrical resistivity of the cleaning water.

3. A monitoring device as claimed in claim 2, wherein said cleaning water is ultra-pure water whose resistivity is not less than 10 k$\Omega$·cm.

4. A monitoring device as claimed in claim 3, wherein the cleaning operation by the cleaning means is continued until the resistivity of the cleaning water as determined by the resistivity meter means rises to a level of not less than 5 k$\Omega$·cm.

5. A monitoring device as claimed in claim 1, wherein said receiver-container means has a form of a funnel, and said cleaning means comprises: a doughnut-shaped shower generator disposed above the funnel-shaped receiver-container, and cleaning water supply source coupled to the shower generator via a pipe having a valve interposed at an intermediate portion thereof.

6. A monitoring device as claimed in claim 1, wherein said rain gauge is coupled to a bottom portion of said receiver-container means, and said cleaning evaluation means is coupled to said rain gauge means via a pipe having a valve interposed at an intermediate portion thereof.

7. A monitoring device as claimed in claim 1, wherein said measurement and analysis means is coupled to said rain gauge means via a pipe having a valve interposed at an intermediate portion thereof.

8. A monitoring device as claimed in claim 1, wherein the cleaning water is stored in the receiver-container means and the rain gauge means during intervals of time between a time at which an end of a rainfall is detected by the rainfall sensor means and a time at which a commencement of a next rainfall is detected by the rainfall sensor means.

* * * * *